United States Patent
Singh et al.

(10) Patent No.: US 7,122,198 B1
(45) Date of Patent: Oct. 17, 2006

(54) FAST DISSOLVING COMPOSITION WITH PROLONGED SWEET TASTE

(75) Inventors: Amarjit Singh, New Delhi (IN); Rajesh Jain, New Delhi (IN)

(73) Assignee: Panacea Biotec Limited, New Delhi (IN)

( * ) Notice: Subject to any disclaimer, the term of this patent is extended or adjusted under 35 U.S.C. 154(b) by 1 day.

(21) Appl. No.: 10/148,651

(22) PCT Filed: Nov. 24, 2000

(86) PCT No.: PCT/IN00/00113

§ 371 (c)(1),
(2), (4) Date: Aug. 19, 2002

(87) PCT Pub. No.: WO01/39749

PCT Pub. Date: Jun. 7, 2001

(30) Foreign Application Priority Data

Nov. 30, 1999 (IN) .............................. 1514/DEL/99

(51) Int. Cl.
*A61K 9/00* (2006.01)
*A61K 9/20* (2006.01)
*A61K 9/22* (2006.01)

(52) U.S. Cl. ..................... 424/401; 424/464; 424/465; 424/479; 424/484

(58) Field of Classification Search ................ 424/400, 424/441, 497, 430, 427, 401, 464, 465, 479, 424/484; 514/819, 785
See application file for complete search history.

(56) References Cited

U.S. PATENT DOCUMENTS 5,939,091 A * 8/1999 Eoga et al. ................. 424/441
6,048,541 A * 4/2000 Misra et al. ................ 424/401
6,248,363 B1 * 6/2001 Patel et al. ................. 424/497

FOREIGN PATENT DOCUMENTS

| EP | 0229000 | 7/1987 |
| EP | 0452268 | 10/1991 |
| FR | 2766089 | 1/1999 |

* cited by examiner

*Primary Examiner*—Johann Richter
*Assistant Examiner*—Mina Haghighatian
(74) *Attorney, Agent, or Firm*—Ladas and Parry LLP

(57) ABSTRACT

A novel fast dissolving pharmaceutical composition in solid dosage form with prolonged sweet taste which comprises (a) At least one pharmaceutically active agent, (b) At least one water soluble sugar, (c) At least one non-sugar sweetner in normal fast release form and (d) At least one non-sugar sweetner in a mucoadhesive slow release form.

7 Claims, No Drawings

FAST DISSOLVING COMPOSITION WITH PROLONGED SWEET TASTE

INTRODUCTION

The present invention is related to a novel composition of a Fast dissolving pharmaceutical preparation in solid dosage form with prolonged sweet taste and a process for the manufacture thereof.

BACKGROUND OF THE INVENTION

Generally, solid pharmaceutical preparation such as tablets/capsules are designed so that after oral administration, they disintegrate or dissolve in the digestive organs and the active ingredients are absorbed. Such compositions are not meant to disintegrate or dissolve in the oral cavity.

However, in certain conditions there is a requirement of fast disintegrating or dissolving tablets which can be administered even without water. Such fast dissolving tablets disperse readily to form a suspension or solution of the drug after mixing with the saliva, which is easily swallowed by the patients. These are particularly suitable for children or aged patients who have difficulty in chewing and/or swallowing an intact tablet/capsule.

Fast mouth dissolving tablets are also suitable for those patients:—
a) Who are suffering from nausea or vomiting;
b) Who have an upper gastrointestinal tract disease e.g., injury in food pipe;
c) Who have undergone upper GI surgery;
d) Who are prostrate;
e) Who are elderly and have frequent urination problems at night.
f) Who are incapacitated elderly patients e.g. suffering from Parkinson's disease;
g) Who are children;
h) Who are in a situation where water is not available.

All the above conditions necessitate that solid dosage form like tablets and capsules should be modified to accommodate above conditions. Formulating conventional tablets and liquid dosage forms does not solve all the problems stated above. Dispersible tablets still require water and lead to gritty suspensions. Such reconstituted dosage forms as well as ready-made suspensions still cannot be given in all above conditions and additionally they pose problems of uniformity of doses and stability of the drug.

In the past, techniques have been reported for producing such fast dissolving tablets, but most of them require the use of highly specialized manufacturing processes or specialized packaging. The Zydis technology from R. P. Scherer, England for instance, utilizes freeze drying of active ingredient with polymer, sugar and other ingredients to form a fast dissolving dosage form. (Manuf. Chemist. February, 1990). European Patent Application No. EP 0 839 526 A2 describes the use of a high cost excipient i.e. erythritol in combination with an active ingredient, crystalline Cellulose and disintegrants to prepare fast disintegrating buccal tablets. U.S. Pat. No. 5,073,374 discloses a fast dissolving buccal tablet containing an active ingredient, a water soluble sugar such as sorbitol and a lubricant. U.S. Pat. No. 5,085,876 discloses a surprisingly fast dissolving sweetening agent in combination with caramel.

U.S. Pat. No. 5,466,464 discloses a solid preparation soluble in buccal cavity containing agar in combination with sugars like lactose and/or mannitol and an active ingredient. The drawback in this preparation is that agar is a natural material susceptible to variability and microbial contamination. The composition described in U.S. Pat. No. 5,720,974 requires a special "Compression-Molding" process to produce fast dissolving tablet. U.S. Pat. No. 5,837,285 discloses fast soluble tablets which are produced by a novel process which involves the compression shaping of a wet kneaded mass of drug and sugar alcohol. The wet tablets produced are thereafter dried.

Another U.S. Pat. No. 5,869,098 discloses fast dissolving compressed tablets manufactured by using partially hygroscopic shearform matrices. Such matrices are prepared from sugar carriers using a flash-heat process. Further U.S. Pat. No. 5,112,616 discloses the use of solid selected from polyethylene glycols and glycerides, wherein glycerides melt in the range of 25° C. to 45° C. surfactants selected from the groups consisting of nonionic Poly (oxypropylene) Poly (oxyethylene) copolymers, polyoxyethylene polysorbate derivatives and sodium lauryl sulfate to prepare fast dissolving buccal tablets.

PCT Application Number WO 93/23017 defines a fast dissolving matrix consisting of gelatin, pectin and/or soy fiber protein and one or more amino acids having from 2 to 12 carbon atoms.

All the compositions disclosed in the prior art suffer from the drawback of a bitter taste in the mouth after consumption and also do not provide for a prolonged sweet taste in oral cavity after consumption of such fast dissolving compositions.

It is the object of the present invention to provide a pharmaceutical preparation in solid dosage form, preferably in the form of a compressed tablet which when orally administered dissolves or disperses in the mouth within one minute requiring very little amount of body fluids like saliva to produce a smooth solution or suspension of the drug with a prolonged sweet taste.

Accordingly the present invention relates to a novel fast dissolving pharmaceutical composition in solid dosage form with a prolonged sweet taste which comprises:
a) at least one pharmaceutically active agent in an amount of from 0.1 to 99 weight % of the total dosage form;
b) at least one water soluble sugar in an amount of from 5 to 95 weight % of the total dosage form;
c) at least one non-sugar sweetener in a fast release form in an amount of from 0 to 10 weight % of the total dosage form; and
d) at least one non-sugar sweetener in a mucoadhesive slow release form in an amount of from 0.5 to 20 weight % of the total dosage form.

The present invention also relates to a process for the preparation of a fast dissolving pharmaceutical composition in solid dosage form with a prolonged sweet taste which consists essentially of mixing the following ingredients:
a) at least one pharmaceutically active agent in an amount of from 0.1 to 99 weight % of the total dosage form;
b) at least one water soluble sugar, in an amount of from 40 to 95 weight % of the total dosage form;
c) at least one non-sugar sweetener in a fast release form in an amount of from 0 to 10 weight % of the total dosage form;
d) at least one non-sugar sweetener in a mucoadhesive slow release form in an amount of from 0.5 to 20 weight % of total dosage form;

and compressing the resulting mixture obtained into tablets or any other solid dosage form.

The water soluble sugars which can be used in the process according to the present invention are Mannitol, Sorbitol, Xylitol and/or the like.

The non-sugar sweeteners which can be used in the process according to the present invention are Aspartame, Acesulfame potassium, Saccharin sodium, Cyclamates, Glycirrhizin and/or the like.

The non-sugar sweetener in a mucoadhesive slow release form is obtained by mixing, coating, granulating, encapsulation, matrix formulation or complexation of a non-sugar sweetener with a mucoadhesive agent as stated herein.

The drugs, pharmaceutically active agents or their salts to be employed for the fast dissolving buccal tablet in accordance with the present invention can be selected from the following group of drugs α-ADRENERGIC AGONIST such as Adrafinil, Adrenalone, Amidephrine, Apraclonidine, Budralazine, Clonidine, Cyclopentamine, Detomidine, Dimetofrine, Dipivefrin, Ephedrine, Epinephrine, Fenoxazofine, Guanabenz, Guanfacine, Hydroxyamphetamine, Ibopamine, indanazoline, tsometheptene, Mephentermine, Metaraminol, Methoxamine, Methylhexaneamine, Metizoline, Midodrine, Naphazoline, Norepinephrine, Norfenefrine, Octodrine, Octopamine, Oxymetazoline, Phenylephrine, Phenyfpropanolamine, Phenylpropylmethylamine, Pholedrine, Propylhexedrine, Pseudoephedrine, Rilmenidene, Synephrine, Tetrahydrozo(ine, Tiamenidine, Tramazoline, Tuaminoheptane, Tymazoline, Tyramine, Xylometazoline.

β-ADRENERGIC AGONIST such as Formoterol, Methoxyphenamine, Ritodrine, Terbuterol.

α-ADRENERGIC BLOCKER such as Dapiprazole, Doxazosin, Ergoloid, Mesylates, Fenspiride, Prazosin, Terazosin, Tolazoline, Yohimbine α-ADRENERGIC BLOCKER such as Acebutolol, Amosulalof, Arotinolol, Atenolol, Befunolol, Betaxolol, Bevantolol, Bisoprolol, Bopindofol, Bucumofol, Bufetolol, Buforalol, Bunitrolol, Bupranolol, Butofilolol, Carazolol, Carteolol, Carvedilol, Celiprolo(, Cetamolol, Cloranolol, Dilevalol, Epanolol, Esmolol, Indenolol, Labetalol, Levobunolol, Mepindolol, Metipranolol, Metoprolol, Moprolol, Nadolol, Nadoxolol, Nifenalol, Nipradilol, Oxprenolol, Penbutolol, Pindolol, Practolol, Propranolol, Sotalol, Sulfinalol, Tafinolol, Tertatolol, Timolol, Toliprolol, Xibenolol.

ALCOHOL DETERRENT such as calcium cyanamide citrated, Disulfiram, Nitrefazofe ALDOSE REDUCTASE INHIBITOR such as Epairestat, Ponalrestat, Sorbinil, Tolrestat ANABOLIC such as Androisoxazole, Androstenediol, Bolandiol, Bolasterone, Clostebol, Ethylestrenol, Formyldienolone, 4-Hydroxy-19-nortestosterone, Methandriol, Methenolone, Methyltrienolone, Nandrolone decanoate, Nandrolone P.-Hexyloxyphenyl-propionate, Nandrolone Phenpropionate, Norbolethone, Oxymesterone, Quinbolone, Stenbolone, Trenbolone, ANALGESIC (DENTAL) such as Chlorobutanol, Clove, Eugenol, Potassium Nitrate, Potassium Oxalate.

ANALGESIC (NARCOTIC) such as Alfentanil, Allylprodine, Alphaprodine, Anileridine, Benzylmorphine, Bezitramide, Buprenorphine, Butorphanol, Clonitazene, Codeine, Desomorphine, Dextromoramide, Dezocine, Diampromide, Dihydrocodeine, Dihydrocodeinone Enol Acetate, Dihydromorphine, Dimenoxadol, Dimepheptanol, Dimethylthiambutene, Dioxaphetyl butyrate, Dipipanone, Eptazocine, Ethoheptazine, Ethylmethylthiambutene, Ethylmorphine, Etonitazene, Fentanyl, Hydrocodone, Hydromorphone, Hydroxypethidine, Isomethadone, Ketobemidone, Levorphanol, Lofentanil, Meperidine, Meptazinol, Metazocine, Methadone, Metopon, Morphine, Morphine Derivatives, Myrophine, Nalbuphine, Narceine, Nicomorphine, Norlevorphanol, Normethadone, Normorphine, Norpipanone, Opium, Oxycodone, Oxymorphone, Papaveretum, Pentazocine, Phenadoxone, Phenazocine, Phenoperidine, Piminodine, Piritramide, Proheptazine, Promedol, Properidine, Propiram, Propoxyphene, Sufentanil, Tilidine.

ANALGESIC (NON-NARCOTIC) such as Acetaminophen, Acetaminosalol, Acetanilide, Acetylsalicylates, Acetylsalicylic Acid, Aceclofenac, Alminoprofen, Aloxiprin, Aluminum Bis (acetylsalicylate), Aminochlorthenoxazin, 2-Amino-4-picoline, Aminopropylon, Aminopyrine, Antipyrine, AntipyrinP Salicylate, Antrafenine, Apazone, Aspirin, Benorylate, Benoxaprofen, Benzpiperylon, Benzydamine, p-Bromoacetanilide, 5-Bromosalicylic Acid Acetate, Bufexamac, Bucetin, Bumadizon, Butacetin, Carbamazepine, Carbetidine, Carbiphene, Carsalam, Chloralantipyrine, Chlorthenoxazin(e), Cholin salicylate, Cinchophen, Ciramadol, Clometacin, Cropropamide, Crotethamide, Dexoxadrol, Difenamizole, Diflunisal, Dipyrocetyl, Dipyrone, Emorfazone, Enfenamic Acid, Epirizole, Etersalate, Ethenzamide, Ethoxazene, Etodolac, Felbinac, Fenoprofen, Floctafenine, Flufenamic Acid, Fluoresone, Flupirtine, Fluproquazone, Flurbiprofen, Fosfosal, Gentisic Acid, Glafenine, Ibufenac, Imidazole Salicylate, Indomethacin, Indoprofen, Isofezolac, Isoladol, Isonixin, Ketoprofen, Ketorolac, p-Lactophenetide, Lefetamine, Loxoprofen, Lysine Acetylsalicylate, Methotrimeprazine, Metofoline, Miroprofen, Morazone, Morpholine Salicylate, Naproxen, Nefopam, Nifenazone, 5' Nitro-2'Propoxyacetanilide, Parsalmide, Perisoxal, Phenacetin, Phenazopyridine, Phenocoll, Phenopyrazone, Phenyl Acetylsalicylate, Phenyl salicylate, Phenyramidol, Pipebuzone, Piperylone, Prodilidine, Propacetamol, Propyphenazone, Proxazole, Quinine Salicylate, Ramifenazone, Rimazolium metisulfate, Salacetamide, Salicin, Salicylamide O-acetic acid, Salicylic Acid, Salicylates and derivatives, Salicylsulfuric Acid, Salsalate, Salverine, Simetride, Sulfamipyrine, Suprofen, Talniflumate, Tenoxicam, Terofenamate, Tetrandrine, Tinoridine, Tolfenamic Acid, Tolpronine, Tramadol, Viminol, Xenbucin, Zomepirac ANDROGEN such as Boldenone, Fluoxymesterone, Mestanolone, Mesterolone, Methandrostenolone, 17-Methyltestosterone, 17a-Methyl-testosterone 3-cyclopentyl Enol Ether, Norethandrolone, Normethandrone, Oxandrolone, Oxymetholone, Prasterone, Stanolone, Stanozolol, Testosterone, Testosterone 17-Chloral Hemiacetal, Testosterone 17.-Cypionate, Testosterone Enanthate, Testosterone nicotinate, Testosterone Phenylacetate, Testosterone Propionate, Tiomesterone, ANESTHETIC such as Acetamidoeugenol, Alfadolone acetate, Alfaxalone; Ambucaine. Amolanone, Amylocalne, Benoxinate, Betoxycaine, Biphenamine, Bupivacaine, Burethamine, Butacaine, Butamben, Butanilicaine, Buthalital, Butoxycaine, Carticaine, 2-Chloroprocaine, Cocaethylene, Cocaine, Cyclomethycaine, Cocaethylene, Dibucaine, Dimethisoquin, Dimethocaine, Diperodon, Dyclonine, Ecgonidine, Ecgonine, Ethyl Aminobenzoate, Ethyl Chloride, Etidocaine, Etoxadrol, P-Eucaine, Euprocin, Fenalcomine, Fomocaine, Hexobarbital, Hexylcaine. Hydroxydione, Hydroxyprocaine. Hydroxytetracaine, isobutyl p-Aminobenzoate, Ketamine, Leucinocaine Mesylate, Levoxadrol, Lidocaine, Mepivacaine, Meprylcaine, Metabutoxycaine, Methohexital, Methyl Chloride, Midazolam, Myrtecaine, Naepaine, Octacaine, Orthocaine, Oxethazaine, Parethoxycaine, Phenacaine, Phencylidine. Phenol, Piperocaine, Piridocaine, Polidocanol, Pramoxine, Prilocalne, Procaine, Propanidid, Propanocaine, Proparacaine, Propipocaine, Propofol, Propoxycaine, Pseudococaine. Pyrrocaine, Risocaine, Salicyl Alcohol, Tetracaine, Thialbarbital, Thiamylal, Thiobutabarbital, Thiopental, Tolycaine, Trimecaine, Zolamine.

ANOREXIC such as Aminorex, Amphecloral, Benzphetamine, Chlorphentermine, Clobenzorax, Cloforex, Cyclexedrine, Di phemethoxidine, Fenbutrazate, Fenfluramine, Fenproporex, Furfurylmethylamphetamine, Levophacetoperane, Mefenorex, Metamfepramone, Norpseudoephedrine, Phenpentermine, Picilorex ANTHELMINTIC.

(CESTODES) such as Arecoline, Aspidine, Aspidinol, Dichlorophen(e), Embelin, Kosin, Naphthalene, Niclosamide, Pelletierine, Pelletierine tannate, Quinacrine.

Anthelmintic (NEMATODES) such as Alantolactone, Amoscanate, Ascaridole, Bephenium, Bitoscanate, Carbon Tetrachloride, Carvacrol, Cyclobendazole, Diethylcarbamazine, Diphenane, Dithiazanine Iodide, Dymanthine, Gentian Violet, 4Hexylresorcinol, Kainic Acid, Mebendazole, 2-Naphthol, Oxantel, piperazines, Pyrantel, Pyrvinium Pamoate, a-Santonin, Stilbazium Iodide, Tetrachloroethylene, Thiabendazole, Thymol, Thymyl N-Isoamylcarbamate, Triclofenol piperazine, Urea Stibamine.

ANTHELMINTIC (ONCHOCERCA) such as Ivermectin

ANTHELMINTIC (SCHISTOSOMA) such as Amphotalide, Antimony(s) and Derivatives, Becanthone. Hycanthone, Lucanthone, Niridazole, Oxamniquine, Praziquantel, Stibocaptate, Stibophen.

ANTHELMINTIC (TREMATODES) such as Anthiolimine

ANTIACNE such as Algestone acetophenide, Azelaic Acid, Benzoyi Peroxide, Dichloroacetic acid, Motretinide, Retinoic Acid, Tetroquinone.

ANTIALLERGIC such as Amlexanox, Astemizole, Azelastine, Cromolyn, Fenpiprane, Histamine, Ketotifen, Nedocromil, Oxatomide, Pentigetide, Poison Ivy Extract, Poison Oak Extract, Poison Sumac Extract, Repirinast, Tiaramide, Tranilast, Traxanox, Urushiol, Cetirizine, Fexofenadine.

ANTIAMEBIC such as Arsthinol, Bialamicol, Carbarsone, Cephaeline, Chlorbetamide, Chlorphenoxamide, Dehydroemetine, Dibromopropamidine, Diloxamide, Diphetarsone, Emetine, Fumagillin, Glaucarubin, Glycobiarsol, 8-Hydroxy-7-iodo-5-quinoline sulfonic acid, Iodochlorhydroxyquin, Iodoquinol, Paromomycin, Phanquinone, Phenarsone, Sulfoxylate, Polybenzarsol, Propamidine, Quinfamide, Secnidazole, Sulfarside. Teclozan, Thiocarbarsone, Thiocarbasone, Timidazole.

ANTIANDROGEN such as Bifluranol, Cyoctol, Cyproterone, Oxendolone

ANTIANGINAL such as Amlodipine, Amyl Nitrate, Cinepazet Maleate, Imolamine, Isosorbide Dinitrate, Limaprost, Molsidomine, Nitroxyalklamide Derivatives ANTIARRHYTHMIC such as Acecainide, Adenosine, Ajmaline, Alprenolol, s-Aminoalkyl-s-Arylsulfoximines, Amoproxan, Aprindine, Bretylium Tosylate, Bucumolol, Bunaftine, Butidrine, Butobendine, Capobenic Acid, Cifenline, Disopyramide, Encainide, Flecainide, Hydroquinidine, Indecainide, Ipratopium, Lorajmine, Lorcainide, Meobentine, Mexiletine, Moricizine, Pirmenol, Prajmaline, Procainamide, Pronethalol, Propafenone, Pyrinoline, Quinidine, Quinidine Sulfate, Tocainide, Viquidil.

ANTIARTERIOSCLEROTIC such as Pyridinol Carbamate

ANTIARTHRITIC/ANTIRHEUMATIC such as Allocupreide Sodium, Auranofin, Aurothioglucose, Aurothioglycamide, Azathioprine, Di-tert-Butyl-phenols, Calcium 3-Aurothio-2-propanol-1-sulfonate, Clobuzarit, Cuproxoline, Diacerein, Glucosamine, Gold Sodium Thiosulfate, Hydroxychloroquine, Kebuzone, Lobenzarit, Melittin, Myoral, Penicillamine Antibacterial (Antibiotic)

Aminoglycosides such as Amikacin, Apramycin, Arbekacin, Bambermycins, Butirosin. Dibekacin, Dihydrostreptomycin, Fortimicin(s), Fradiomycin, Gentamicin, Isepamicin. kanamycin, Micronomicin, Neomycin, Neomycin Undecylenate, Netilmicin. Paromomycin, Ribostamycin, Sisomicin, Spectinomycin, Streptomycin, Streptonicozid, Tobramycin Amphenicols such as Azidamfenicol, Chloramphenicol, Chloramphenicol Palmitate, Chloramphenicol Pantothenate, Florfenicol, Thiamphenicol, Ansamycins such as Rifamide, Rifampin, Rifamycin, Rifaximin, Rifapentene β-Lactams Carbapenems such as Imipenem Cephalosporins, such as 1-Carba(dethia)Cephalosporin, Cefaclor, Cefadroxil, Cephalosporins, Cefatrizine, Cefazedone, Cefazolin, Cefixime, Cefinenoxime, Cefodizime, Cefonicid, Cefoperazone, Ceforamide, Cefotaxime, Cefotiam, Cefpimizole, Cefpiramide, Cefpodoxime Proxetil, Cefroxadine, Cefsulodin, Ceftazidime, Cefteram, Ceftezole, Ceftibuten, Ceftizoxime, Ceftriaxone, Cefuroxime, Cefuzonam, Cephacetrile, Sodium, Cephalexin, Cephaloglycin, Cephaloridine, Cephalosporin C, Cephalothin, Cephapirin sodium, Cephradine, Pivcefalexin Cephamycins such as Cefbuperazone, Cefinetazole, Cefminox, Cefotetan, Cefoxitin Manobactams such as Aztreonam, carumonam, Tigemonam Oxacephems such as Flomoxef, Moxolactam Penicillins such as Amidinocillin, Amdinocillin pivoxil, Amoxicillin, Ampicillin, Apalcillin, Aspoxicillin, Azidocillin, Aziocillin, Bacampicillin, Benzylpenicillinic Acid, Benzylpenicillin, Carbenicillin, Carfecillin, Carindacillin, Clometocillin, Cloxacillin, Cyclacillin, Dicloxacillin, Diphenicillin, Epicillin, Fenbenicillin, Floxicillin, Hetacillin, Lenampicillin, Metampicillin, Methicillin, Meziocillin, Nafcillin, Oxacillin, Penamecillin, Penethamate Hydriodide, Penicillin G Benethamine, Penicillin G Benzathine, Penicillin G Benzhydrylamine, Penicillin G Calcium, Penicillin G Hydrabamine, Penicillin G Potassium, Penicillin G Procaine. Penicillin N, Penicillin O, Penicillin V, Penicillin V Benzathine, Penicillin V Hydrabamine, Penimepicycline, Phenethicillin, Piperacillin, Pivampicillin, Propicillin, Quinacillin, Sulbenicillin, Talampicillin, Temocillin, Ticarcillin Lincosamides such as clindamycin, Lincomycin Macrolides such as Azithromycin, Carbomycin, Clarithromycin, Erythromycin(s) and Derivatives, Josamycin, Leucomycins, Midecamycins, Miokamycin, Oleandomycin, Primycin, Rosaramicin, Roxithromycin, Spiramycin, Troleandomycin, Polypeptides such as Amphomycin, Bacitracin, Capreomycin, Colistin, Enduracidin, Enviomycin, Fusafungine, Gramicidin(s), Gramicidin S, Mikamycin, Polymyxin, Polymyxin B-Methane sulfonic acid, Pristinamycin, Ristocetin, Teicoplanin, Thiostrepton Tuberactinomycin, Tyrocidine, Tyrothricin, Vancomycin, Viomycin(s), Virginiamycin, Zinc Bacitracin Tetracyclines such as Apicycline, Chlortetracycline, Clomocycline, Demeclocycline, Guamecycline, Lymecycline, Meclocycline, Methacycline, Minocycline, Oxytetracycline, Penimepicycline, Pipacycline, Rolitetracycline, Sancycline, Senociclin, Tetracycline Others Such as Cycloserine, Mupirocin, Tuberin Antibacterial (Synthetic)

2,4-Diaminopyrimidines such as Brodimoprim, Tetroxoprim, Trimethoprim

Nitrofurans such as Furaltadone, Furazolium, Nifuradene, Nifuratel, Nifurfoline, Nifurpirinol, Nifurprazine, Nifurtoinol, Nitrofurantoin Quinolones and Analogs such as Amifloxacin, Cinoxacin, Ciprofloxacin, Difloxacin, Enoxacin, Fleroxacin, Flumequine, Lomefloxacin, Miloxacin, Nalidixic Acid, Norfloxacin, Ofloxacin, Oxolinic acid, Pfloxacin, Pipemidic Acid, Piromidic Acid, Rosoxacin, Temafloxacin Sulfonamides such as Acetyl Sulfamethoxypyrazine, Acetyl Sulfisoxazoie, Azosulfamide, Benzylsulfamide, Chloramine-B, Chloramine-T, DichloramineT, Formosulfathiazole, N2-Formyl-Sulfisomidine, N 4-O-D-Glucosylsulfanilamide, Mafenide, 4'-(Methyl-sulfamoyl) sulfanilanilide, p-Nitrosulfathiazole, Noprylsulfamide, Phthalylsulfacetamide, Phthalylsulfathiazole, Salazosufadimidine, Succinylsulfathiazole, Sulfabenzamide, Sulfacetamide. Sulfachlorpyridazine, Sulfachrysoidine, Sulfacytine, Sulfadiazine, Sulfadicramide, Sulfadimethoxine, Sulfadoxine, Sulfaethidole, Sulfaguanidine, /Sulfaguanol, Sulfalene, Sulfaloxic acid, Sulfamerazine, Sulfameter, Sulfamethazine, Sulfamethizole, Sulfamethomidine, Sulfamethoxazole, Sulfamethoxypyridazine, Sulfametrole, Sulfamidochrysoidine, Sulfamoxole, Sulfanilamide, Sulfanilamidomethanesulfonic acid, Triethanolamine Salt, 4-Sulfanilamidosalycylic acid, $N^4$-Sulfanilylsulfanilamide, Sulfanilylurea, N-Sulfanilyl-3,4 xylamide, Sulfanitran, Sulfaperine, Sulfaphenazole, Sulfaproxyline, Sulfapyrazine, Sulfapiridine, Sulfasomizole, Sulfasymazine, Sulfathiozole, Sulfathiourea, Sulfatolamide, Sulfisomidine, Sulfisoxazole Sulfones such as Acedapsone, Acediasulfone, Acetosulfone, Dapsone, Diathimosulfone, Glocosulfone, Solasulfone, Succisulfone, Sulfanilic Acid, p-sulfanilylbenzylamine, p,p-sulfonyldianiline, —N,N'digalactoside, Sulfoxone, Thiazolesulfone Others such as Clofoctol, Hexedine, Magainis, Methenamine Anhydromethylenecitrate, Methenamine Hippurate, Methenamine Mandelate, Methenamine Sulfosalicylate, Nitroxoline, Squalamine, Xibornol ANTICHOLINERGIC Such as Adiphenine, Alverine, Ambutonium, Aminopentamide, Amixetrine, Amprotropine phosphate, Anisotropine methylbromide, Apoatropine, Atropine, Atropine N-Oxide, Benactyzine, Benapryzine, Benzetimide, Benzilonium, Benztropine mesylate, Bevonium Methyl Sulfate; Biperiden, Butropium N-Butyiscopolammonium Bromide, Buzepide, Camylofine, Caramiphen, Chlorbenzoxamine, Chlorphenoxamine, Cimetropium, Clidinium, Cyclodrine, Cyclonium, Cyclopentolate, Cycrimine, Deptropine, Dexetimide, Dibutoline Sulfate, Dicyclomine, Diethazine, Difemerine, Dihexyverine, Diphemanil methylsulfate, N-(1,2Diphenylethyl) nicotinamide, Dipiproverine, Diponium, Emepronium, Endobenzyline, Ethopropazine, Ethybenztropine, Ethylbenzhydramine, Etomidoline, Eucatropine, Fenpiverinium, Fentonium, Flutropium, Glycopyrrolate, Heteronium, Hexocyclium Methyl Sulfate, Homatropine, Homatropine Methyl Bromide, Hyoscyamine, Ipratropium, Isopropamide, Levomepate, Mecloxamine, Mepenzolate, Metcaraphen, Methantheline, Methixene, Methscopoiamine, Octamylamine, Oxybutynin, Oxyphencyclimine, Oxyphenonium, Pentapiperide, Penthienate, Phencarbamide, Phenglutarimide, Pipenzolate, Piperidolate, Piperilate, Poldine methylsulfate, Pridinol, Prifinium, Propyromazine, Scopolamine N-Oxide, Stilonium, Stramonium, Sultroponium, Thihexinol, Thiphenamil, Tiemonium, Timepidium, Tiquizium, Tridihexethyl Iodide, Trihexyphenidyl hydrochloride, Tropacine, Tropenzile, Tropicamide, Trospium, Valethamate, Xenytropium ANTICONVULSANT such as Acetylpheneturide, Albutoin, Aloxidone, Aminoglutethimide, 4-Amino-3-hydroxybutyric Acid, Atrolactamide, Beclamide, Buramate, Carbamazepine, Cinromide, Clonazepam, Decimemide, Diethadione, Dimethadione, Doxenitoin, Eterobarb, Ethadione, Ethosuximide, Ethotoin, Fluresone.

5-Hydroxytryptophan, Lamotrigine, Magnesium Sulfate, Mephenyloin, Metharbital, Methetoin, Methsuximide, 5-Methyl-5-(3-phenanthryl)-hydantoin, 3-Methyl-5Phenyl-hydantoin, Narcobarbital, Nimetazepam, Nitrazepam, Paramethadione, Phenacemide, Pheneturide, Phensuximide, Phenyloin, Phethenylate Sodium, Primidone, Progabide, Solanum, Strontium, Suclofenide, Sulthiame, Tetrantoin, Trimethadione, Valproic Acid, Valpromide, Vigabatrin, Zonisamide.

Antidepressant

Bicyclics such as Binedaline, Caroxazone, Citalopram, Dimethazan, Indalpine, fencamine, Indeloxazine, Nefopam, Nomifensine, Oxitriptan, Oxypertine, Paroxetine, Sertraline, Thiazesim, Trazodone, Zometapine, Hydrazides/Hydrazines such as Benmoxine, Iproclozide, Iproniazid, Isocarboxazid, Nialamide, Octamoxine, Pheneizine.

Pyrrolidones such as Cotinine, Rolicyprine, Rolipram.

Tetracyclics such as Maprotiline, Metralindole, Mianserin, Oxaprotiline. Tricyclics such as Adinazolam, Amitriptyline, Amitriptylinoxide, Amoxapine, Butriptyline, Clomipramine, Demexiptiline, Desipramine, Dibenzepin, Dimetacrine, Dothiepin, Doxepin, Fluacizine, Imipramine, Imipramine N-Oxide, Iprindole, Lofepramine, Melitracen, Metapramine, Nortriptyline, Noxiptilin, Opipramol, Propizepine, Protriptyline, Quinupramine, Tianeptine, Trimipramine Others such as Benactyzine, Bupropion, Butacetin, Deanol, Deanol Aceglumate, Deanol Acetamidobenzoate, Dioxadrol, etoperidone, Febarbamate, Femoxetine, Fenpentadiol, Fluoxetine, Fluvoxamine, Hematoporphyrin, Hypericin, Levophacetoperane, Lithium Medifoxamine, Minaprine, Moclobemide, Oxaflozane, Piberaline, Polycyclic Imides, Prolintane, Pyrisuccideanol, Rubidium, Sulpiride, Sultopride, Teniloxazine, Thozalinone, Tofenacin, Toloxatone, Tranylcypromine, L-Tryptophan, Viloxazine, Zimeldine.

Antidiabetic

Biguanides such as Buformine, Metformin, Phenformin.

Sulfonylurea Derivatives such as Acetohexamide, 1-Butyl-3-metanilylurea, Carbutamide. Chlorpropamide, Glibornuride, Gliclazide, Glipizide, Gliquidone, Glisoxepid, Glyburide, Glybuthiazol(e), Glybuzole, Glyhexamide, Glymidine, Giypinamide, Phenbutamide, Tolazamide, Tolbutamide, Tolcyclamide Others such as Acarbose, Benzylthiazolldone-2,4-dione, Calcium Mesoxalate, Miglitol.

ANTIDIARRHEAL such as Acetyltannic Acid, albumin Tannate, Alkofanone, Aluminium Salicylates, Catechin, Difenoxin, diphenoxylate, Lidamidine, Loperamide, Mebiquine, Trillium, Uzarin.

ANTIDIURETIC such as Desmopressin, felypressin, Lypressin, Ornipressin, Oxycinchophen, Terlipressin, Vasopressin.

ANTIESTROGEN such as Delmadione Acetate, Ethamoxytriphetol, Tamoxifen, Toremifene Antifungal (Antibiotics)

Polyenes such as Amphotericin-B, Candicidin, Dermostatin, Filipin, Fungichromin, Hachimycin, Hamycin, Lucensomycin, Mepartricin, Natamycin, Nystatin, Pecilocin, Perimycin.

Others such as Azaserine, Griseofulvin, Oligomycins, Pyrrolnitrin, Siccanin, Tubercidin, Viridin.

Antifungal (Synthetic)

Allylamines such as Naftifine, Tebinafine.

Imidazoles such as Bifonazole, Butoconazole, Chlordantoin, Chlormidazole, Cloconazole, Clotrimazole, Econazole, Enilconazole, Fenticonazole, Isoconazoie, Ketoconazole, Miconazole, Omoconazole, Oxiconazole nitrate, Sulconazole, Tioconazole Triazoles such as Fluconazole, Itraconazole, Terconazole.

Others such as Acrisorcin, Amorolfine, Biphenamine, Bromosalicylchloranilide, Buclosamide, Chlorphenesin, Ciclopirox, Cloxyquin, Coparaffinate. Diamthazole dihydrochloride, Exalamide, Flucytosine, Halethazole, Hexetidine, Loflucarban, Nifuratel, Potassium Iodide, Propionates, Propionic Acid. Pyrithione, Salicyianilide, Sulbentine, Tenonitrozole, Tolciclate,-Tolindate, Tolnaftate, Triacetin, Ujothion, Undecylenic Acid ANTIGLAUCOMA such as Dapiprazoke, Dichlorphenamide, Dipivefrin, Pilocarpine.

ANTIGONADOTROPIN such as Danazol, Gestrinone, Paroxypropione

ANTIGOUT such as Colchicine, Probenecid, Sulfinpyrazone

Antihistamic Alkylamine Derivatives Such as Acrivastine, Bamipine, Brompheniramine, Chlorpheniramine, Dimethindeda, Tolpropamine, Triprolidine Aminoalkyl Ethers such as Bietabanautine, Bromodiphenhydramine, Carbinoxamine, Clemastine, Diphenylpyraline, Doxylamine, Embrammine, Medrylamine, Mephenhydramine, p-Methyldiphenhydramine, Orphenadrine, Phenyltoloxamine, Piprinhydrinate, Setastine Ethylenediamine Derivates Such as Alloclamide, p-Bromtripelennamine, Chloropyramine, Chlorothen, Histapyrrodine, Methafurylene, Methaphenilene, Methapyrilene, Phenbenzamine, Pyrilamine, Talastine, Thenyldiamine, Thonzylamine, Tripelennamine, Zolamine Piperazines such as Cetirizine, Chlorcyclizine, Clocinizine, Hydroxyzine Tricyclies Phenothiazines such as Ahistan, Etymemazine, Fenethazine, N-Hydroxyethyl promethazine, Isopromethazine, Mequitazine, Promethazine, Pyrathiazine, Thiazinamium Methyl Sulfate Others such as Azatadine, Clobenzepam, Cyproheptadine, Deptropine, Isothipendyl, Loratadine, Prothipendyl Others such as Antazoline, Cetoxime, Clemizole, Clobenztropine, Diphenazoline, Diphenhydramine, Mebhydroline, Phenindamine, Terfenadine, Tritoqualine Antihyperlipoproteinemic Aryloxyalkanoic Acid Derivatives such as Bazafibrate, Binifibrate, Ciprofibrate, Clinofibrate, Clofibrate, Clofibric Acid, Etofibrate, Fenofibrate. Gemfibrozil, Nicofibrate. Pirifibrate, Ronifibrate, Simfibrate, Theofibrate Bile Acid Sequesterants such as Cholestyramine Resin, Colestipol, Polidexide HMG CoA Reductases Inhibitors such as Lovastatin, Pravastatin, Simvastatin Nicotinic Acid derivatives Aluminum Nicotinate, Acipimox, Niceritol, Nicoclonate, Nicomol, Oxiniacic Acid Thyroid Hormones/Analogs such as Etiroxate, thyropropic Acid Others such as Acifran, Azacosterol, Benfluorex, P-Benzalbutyramide, Benzodioxole. Carnitine, Chondroitin Sulfate, Clomestone, Detaxtran, Dextran Sulfate Sodium, 5,8, 11,14,17-Eicosapentaenoic Acid, Eritadenine, Farnesylated tetrahydronaphthalenols, Furazabol, Meglutoi, Melinamide, Mytatrienediol, Naphthyltetrahydronaphtyl-diphosphonates, Ornithine, y-Oryzanol, Pentethine, Penataerythritol, Tetraacetate,-Phenylbutyramide, Phylate Acids And Salts, Pirozadil, Probucol, a-Sitosterol, Sultosilic Acid, Tiadenol, Triparanol Antihypertensive Benzothiadiazine Derivatives sich as Althiazide, Bendroflumethiazide, Benzthiazide, Benzylhydrochlorothiazide, Buthiazide, Chlorothiazide, Chlorthalidone, Cyclopenthiazide, Cyclothiazide, Diazoxide, Epithiazide, Ethiazide, Fenquizone, Hydrochlorothiazide, Hydroflumethiazide, Methyclothiazide, Meticrane, Metolazone, Paraflutizide, Polythiazide, Tetrachlormethiazide, Trichlormethiazide N-Carboxyalkyl (peptide/lactam) Derivatives such as Alacepril, Captopril, Cilazapril, Enalapril, Enalaprilat, Fosinopril, Lisinopril, Moveltipril, Perindopril, Quinapril, Ramipril Guanidine Derivatives Bethanidine, Debrisoquin, Guanacline, Guanadrel, Guanazodine, Guanethidine, Guanochlor, Guanoxabenz, Guanoxan Hydrazines/Phthalazines such as Cadralazine, Dihydralazine, Endralazine. Hydracarbazine, Hydralazine, Pheniprazine, Pildralazine, Todralazine Imidazole Derivatives such as Lofexidine, Phentolamine, Tolonidine Quaternary Ammonium Compounds Azamethonium Chlorisondamine. Hexamethonium, Pentacynium bis(methylsulfate), Pentamethonium, Pentolinium Tartate, Phenactropinium, Trimethidinium Methosulfate Quinazoline Derivatives such as Alfuzosin, Bunazosin Reserpine Derivatives such as Bietaserpine, Deserpidine, Rescinnamine, Reserpine, Syrosingopine Sulfanoamide Derivatives such as Ambuside, Clopamide, Furosemide, Indapamide, Quinethazone, Tripamide, Xipamide Others such as Ajmaline, g-Aminobutyric Acid, Bufeniode, Chlorthalidone, Cicletainine, Ciclosidomine, Cryptenamine Tannates, Flosequinan, Indoramin, Ketanserin, Metbutamate, Mecamylamine, Methyldopa, Methyl 4-Pyridyl Ketone Thiosemicarbazone, Metolazone, Minoxidil. Muzolimine, Pargyline Glycine Aminopropargyl Diols, Protoveratrines, Raubasine, Rescimetol, Saralasin, Sodium Nitroprusside, Ticrynafen, Trimethaphan camsylate, Tyrosinase, Urapidil ANTIHYPERTHYROID Such as 2-Amino-4-methylthiazole, 2-Aminothiazole, Carbimazole, 3,5-Dibromo-L-tyrosine, 3,5-Diiodotyrosine, Hinderin, Iodine, lothiouracil, Methimazole, Methylthiouracil, Propylthiouracil, Sodium Perchlorate, Thibenzazoline, Thiobarbital, 2-Thiouracil ANTIHYPOTENSIVE such as Amezinium Methyl Sulfate, Angiotensin Amide, Etifelmin, Etilefrin, Gepefrine ANTIHYPOTHYROID such as Levothyroxine, Liothyronine, Thyroid, Thyroidin, Thyroxine, Tiratricol Anti-Inflammatory (Nonsteroidal)

Aminoarylcarboxylic Acid Derivatives such as Etofenamate, Meclofenamic Acid, Mefanamic Acid, Niflumic Acid Arylacetic Acid Derivatives such as Acemetacin, Amfenac, Cinmetacin, Clopirac, Diclofenac, Fenclofenac, Fenclorac, Fenclozic Acid, Fentiazac, Glucametacin, Isoxepac, Lonazolac, Metiazinic Acid, Oxametacine, Proglumetacin, Sulindac, Tiaramide, Tolmetin Arylbutyric Acid Derivatives such as Butibufen, Fenbufen Arylcarboxylic Acids such as Clidanac, Ketorolac, Tinoradine Arylpropionic Acid Derivatives such as Bucloxic Acid, Carprofen, Fenoprofen, Flunoxaprofen, Ibuprofen, Ibuproxam, Oxaprozin, Piketoprofen, Pirprofen, Pranoprofen, Protizinic Acid, Tiaprofenic Acid Pyrazoles such as Epirizole Pyrazoles such as Mepirizole Pyrazolones such as Clofezone, Feprazone, Mofebutazone, Oxyphenbutazone, Phenylbutazone, Phenyl Pyrazolidininones, Suxibuzone, Thiazolinobutazone Salicylic Acid Derivatives such as Bromosaligenin, Fendosal, Glycol Salicylate, Mesalamine, 1-Naphthyl Salicylate, Olsalazine, Sulfasalazine Thiazinecarboxamides such as Droxicam, Isoxicam, Piroxicam Others such as e-Acetamidocaproic Acid, S-Adenosylmethionine, 3-Amino-4hydroxybutyric Acid, Amixetrine, Bendazac, Bucolome, Carbazones. Difenpiramide, Ditazoi, Guaiazulene, Heterocyclic Aminoalkyl Esters of Mycophenolic Acid And Derivatives, Nabumetone, Nimesulide, Orgotein, Oxaceprol, Oxazole Derivatives Paranyline, Pifoxime, 2-subsitituted-4,6-di-tertiary-butyl-s-hydroxy-1, 3-pyromidines, Proquazone, Sialyl Lewis Dimers, Tenidap ANTIMALARIAL such as Acedapsone, Alphaminoquinolines, 40 Aminoquinolines, Amodiaquin, Arteether, Artemether, Artemisinin, Artesunate, Bebeerine, Chirata, Chlorguamide, Chloroquine, Chlorproguanil, Chinchona, Cinchonidine, Cinchonine, Cycloguanil, Euqinine. Gentiopicrin, Halofantrine, Mefloquine Hydrochloride, 3-Methylarsacetin, Pamaquine, Plasmocid, Primaquine, Pyrimethamine, Quinacrine, Quinine, (Acids, Salts and Derivatives), Quinine Formate, Quinine Gluconate, Quinine Tannate, Quinine Urea Hydrochloride, Quinocide, Quinoform, Quinoline, Sodium Arsenate, Diabasic ANTIMIGRAINE such as Alpropride, Dihydroergotamine, Ergocornine, Ergocorninine, Ergocryptine, Ergot, Ergotamine, Flumedroxone Flumedroxone acetate, Fonazine, Methysergid(e), Oxetorone, Pizotyline, Sumatriptan ANTINAUSEANT such as Acetylleucine Monoethanolamine, Bietanautine, Bromopride, Buclizine, Clebopride, Cyclizine, Dimenhydrinate, Diphenidol, Domperidone, Granisetron, Meclizine, Methallatal, Metoclopramide, Metopimazine, Nabilone, Ondansetron, Oxypendyl, Pipamazine, Piprinhydrinate, Scopolamine, Tetrahydrocannabinols, Thiethylperazine, Trimethobenzamide Antineoplastic Alkyl agents: Alkyl Sulfonates such as Busulfan, Improsulfan, Piposulfan, Aziridines such as Benzodepa, Carboquone, Meturedepa, Uredepa Ethylenimines and Methylmelamines such as Altretamine, Triethylenemelamine, Triethylenephosphoramide, Triethylenethiophosphoramide, Trimethylolmelamine Nitrogen Mustards such as Chlorambucil, Chlornaphazine, Cyclophosphamide, Estramustine, Ifosfamide, Mechlorethamine, Mechlorethamine Oxide Hydrochloride, Melphalan, Novembichin, Phenesterine, Prednimustine, Trofosfamide, Uracil Mustard Nitrosoureas Carmustine, Chlorozotocin, Fotemustine, Lomustine, Nimustine, Ranimustine Others such as Dacrabazine, Mannomustine, Mitobronitol, Mitolactol, Pipobroman Antibiotics such as Aclacinomycins, Actinomycin F1, Anthramycin, Azaserine, Bleomycins, Cactinomycin, Carubicin, Carzinophilin, Chromomycins, Dactinomycin, Daunorubicin, Carzinophilin, Chromomycins, Dactinomycin, Daunorubicin, 6-Diazo-5oxo-L-norleucine, Doxorubicin, Epirubicin, Mitomycins, Mycophenolic Acid, Nogalamycin, Olivomycins, Peplomycin, Plicamycin, Profiromycin, Puromycin, Streptonigrin, Streptozocin, Tubercidin, Ubenimex, Zinostatin, Zorubicin Antimetabolites Folic Acid Analogs such as Denepterin, Methotrexate, Pteropterin, Trimetrexate Purine Analogs such as Fludarabine, 6-Mercaptopurine, Thiamiprine, Thiguanaine Pyrimidine Analogs such as Ancitabine, Azacitidine, 6-Azauridine, Carmofur, Cytarabine, Dibexyuridines, Doxifluridine, Enocitabine, floxuridine, Fluorouracil, Tegafur Enzymes such as L-Asparaginase, Pulmozyme Others such as Aceglatone, Aldophosphamide Glycoside, Aminolevulinic Acid, Amsacrine, Bestrabucil, Bisantrene, Carboplatin, Deformide, Demecolcine, Diaziquone, Elformithine, Ellipitinium Acetate, Etoglucid, Etoposide, Gallium Nitrate, Hydroxyurea, Interferon-a, Interferon-0, Interferon-y, Interleukin-2, Lentinan, Lonidamine, Mitoguazone, Mitoxantrone, Mopidamol, Nitracrine, Pentostatin. Phenamet, Pirarubicin. Podophyllinic Acid, 2-Ethylhydrazide, Procarbazine, PSK®, Razoxane, Sizofiran, Spirogermanium, Taxol, Teniposide, Tenuazonic Acid, Triaziquone, 2,2',2"Trichlorotriethylamine, Urethan, Vinblastine, Vincristine, Vindesine Antineoplastic(Hormonal)

Androgens such as Calusterone, Dromostanolone Propionate, Epitiostanol, Mepitiostane, Testolactone Antiadrenals such as Aminoglutethimide, Mitotane, Trilostane Antiandrogens such as Flutamide, Nilutamide Antiestrogens such as Aromatase Inhibiting 4(5)-Imidazoles Antineoplastic Adjunct Folic Acid Replenisher such as Frolinic Acid ANTIPARKINSONIAN such as Amantadine, Benserazide, Bietanautine, Biperiden. Budipine, Carbidopa, Deprenyl, Dexetimide, Diethazine, Droxidopa, Ethopropazine, Ethylbenzhydramine, Levodopa, Piroheptine, Pridinol, Prodipine, Terguride, Tiapride, Tigloidine ANTIPHEOCHROMOCYTOMA such as Metyrosine, Phenoxybenzamine ANTIPNEUMOCYSTIS such as Eflornithine ANTIPROSTATIC HYPERTROPHY such as Proscar®

ANTIPROTOZOAL (LEISHMANIA) such as Ethylstibamine, Hydroxystilbamidine, N-Methylglucamine, Pentamidine, Stilbamidine ANTIPROTOZOAL (TRICHOMONAS) such as Acetarsone, Aminitrozole, Anisomycin, Azanidazole, forminitrazole, furazolidone, Azanidazole, Lauroguadine, Metronidazole, Nifuratel, Nimorazole, Silver Picrate, Tenonitrozole ANTIPROTOZOAL(TRYPANOSOMA) such as Benznidazole, Eflornithine, L Melarsoprol, Nifurtimox, Oxophenarsine, Puromycin, Quinapyramine, Suramin Sodium, Trypan Red, Tryparsamide ANTIPRURITIC such as Camphor, Cyproheptadine, Dichlorisone, Glycine, Halometasone, 3-Hydroxycamphor, Menthol, Mesulphen, Methdilazine, Phenol, Spirit Of Camphor, Trimeprazine ANTIPSORIATIC such as Acitretin, Anthralin, 6-Azauridine, Bergrapten(e), Chrysarobin, Etretinate, Pyrogallol Antipsychotic Butyrophenones such as Benperidol, Bromperidol, Droperidol, Fluanisone, Haloperidol, Melperone, Moperone, Pipamperone, Spiperone, Timiperone, Trifulperidol Phenothiazines such as Acetophenazine, Butaperazine, Carphenazine, Chlorproethiazine, Chlorpromazine, Clospirazine, Mepazine, Mesoridazine, Methoxypromazine, Metofenazate, Oxflumazine, Perazine, Pericyazine, Perimethazine, Prochlorperazine, Promazine, Sulforidazine, Thiopropazate, Thioridazine, Trifluoperazine, Triflupromazine Thioxanthenes such as Chlorprothixene, Clopenthixol, Flupentixol, Thiothixene Other such as Alizapride, Amisulpride, 4-Arylpiperazines, 4-Arypiperdines, Buramate, Fluspirilene, Molindone, Penfluridol, Pimozide, Spirilene, Sulpiride ANTIPYRETIC such as Aconine, Aconite, Aconitine, Phenicarbazide ANTIRICKETTSIAL such as p-Aminobenzoic Acid ANTISEBORRHEIC such as 3-O-Lauroylpyridoxol Diacetate, Piroctone, Resorcinol, Selenium Sulfides, Tioxolone Antiseptic Guanidines Such as Alexidine, Ambazone, Chlorhexidine, Picloxydine Halogens/Halogen compounds such as Bronyl Chloride, Calcium Iodate, Iodine Monochloride, Iodine Trichloride, Iodoform, Povidone-Iodine, Sodium Hyopchlorite, Sodium Iodate, Symclosene, Thymol Iodide, Triclocarban, Triclosan, Troclosene Potassium Nitrofurans such as Furazolidone, 2-(Meth oxymethyl)-5-Nitrofuran, Nidroxyzone, Nifuroxime, Nifurzide, Nitrofurazone Phenols such as Acetomeroctol, Chloroxylenol, Hexachlorophene, 1-Naphthyl Salicylate, 2,4,6-Tribromom-cresol, 3'4',5-Trichlorosalicylanilide Quinolines such as Aminoquinuride, Chloroxine, Chlorquinadol, Cloxyquin, Ethylhydrocupreine, Halquinol, Hydrastine, 8-Hydroxquinoline Sulfate Others such as Boric Acid, Chloroazodin, m-Cresyl Acetate, Cuperic Sulfate, Ichthammol ANTISPASMODIC such as Alibendol, Ambucetamide, Aminopromazine, Bietamiverine. Butaverine, Butropium, Caroverine, Cimetropium, Cinnamedrine, Clebopride, Coniine hydrobromide, Coniine, Difemerine, Diisopromine, Dioxaphetyl Butyrate, Drofenine, Ethaverine, Feclemine, Fenalamide, Fenoverine, Fenpiprane, Flavoxate, Flopropione. Gluconic Acid, Guaiactamine, Hydramitrazine, Hymecromone, Leiopyrrole, Mebeverine, Moxaverine, Nafiverine, Octaverine, Phenamacide, Phloroglucinol, Pinaverium, Piperilate, Pipoxolan hydrochloride, Pramiverin, Properidine, Propivane, ANTITHROMBOTIC such as Anagrelide, Argatroban, Cilostazol, Daltroban, Defibrotide, Enoxaparin, Fraxipariner®, Indobufen, Lamoparan, Ozagrel, Picotamide, Plafibride, Tedelparin, Ticlopidine, Triflusal.

ANTITUSSIVE such as Allocamide, Amicibone, Benproperine, Benzonatate, Bibenzonium, Bromoform, Butamirate, Butethamate, Caramiphen Ethanedisulfonate, Carbetapentane, Chlophedianol, Clobutinol, Cloperastine, Codeine Methyl Bromide, Codeine N-Oxide, Codeine Phosphate, Codeine Sulfate, Cyclexanone, Dextromethorphan, Dibunate Sodium, Dihydrocodeine, Dihydrocodeinone Eno [Acetate, Dimemorfan, Dimethoxanate a, a-Diphenyl-2-piperidinepropanol, Dropropizine, Drotebanol, Eprazinone, Ethyl Dibunate, Ethylmorphine, Fominoben, Guaiapate, Hydrocodone, Isoaminile, Levopropoxyphene, Morclofone, Narceine, Normethadone Noscapine, Oxeladin, Oxolamine, Pholcodine, Picoperine, Pipazethate, Piperidione, Prenoxdiazine, Racemethorphan, Taziprinon hydrochloride, Tipepidine, Zipeprol ANTITULCERATIVE such as Aceglutamide Aluminum complex, F-Acctamidocaproic Acid Zinc Salt, Acetoxolone, Arbaprostil, Benexate Hydrochloride, Bismuth Subcitrate Sol(Dried), Carbenoxolone, Cetraxate, Cimetidine, Enprostii, Esaprazole, Famotidine, Ftaxilide, Gefarnate, Guaiazulene, Irsogladine, Nizatidine, Omeprazole, Ornoprostil, YOryzanol, Pifamine, Pirenzepine, Plaunotol, Ranitidine, Rioprostil, Rosaprostol, Rotraxate, Roxatidine Acetate, Sofalcone, Spizofurone, Sucralfate, Teprenone, Trimoprostil, Trithiozine, Troxipide, Zolimidine.

ANTIUROLITHIC such as Acetohydroxamic Acid, Allopurinol, Potassium citrate, Succinimide.

ANTIVENIN such as Lyovacr®, Antivenin.

Antiviral

Purines/Pyrimidines such as 2-Acetyl-pyridine 5-((2-pyridylamino) thiocarbonyl), Thiocarbonohydrazone, Acyclovir, Dideoxyadenosine, Dideoxycytidine, Dideoxyinosine, Edoxudine, Floxuridine, Ganciclovir, Idoxuridine, MADU, Pyridinon, Trifluridine, Vidarabine, Zidovudine.

Others such as Acetylleucine, Monoethanolamine, Acridinanamine, Alkylisoxazoles, Amantadine, Amidinomycin, Cuminaldehyde, Thiosemicarbzone, Foscarnet Sodium, Kethoxal, Lysozyme, Methisazone, Moroxydine, Podophyllotoxin, Ribavirin, Rimantadine, stallimycin, statolon, Thymosins, Tromantadine, Xenazoic Acid.

Anxiolytic

Arylpiperazines such as Buspirone, Gepirone, Ipsapirone.

Benzodiazepine Derivatives Alprazolam, Bromazepam, Camazepam, Chlordiazepoxide, Clobazam, Clorazepate, Clotiazepam, Cloxazolam, Diazepam, Ethyl Loflazepate, Etizolam, Fluidazepam, Flutazolam, Flutoprazepam, Halazepam, Ketazolam, Lorazepam, Loxapine, Medazepam, Metaclazepam, Mexazolam, Nordazepam, Oxazepam, Oxazolam, Pinazepam, Prazepam, Tofisopam.

Carbamates such as Cyclarbamate, Emylcamate, Hydroxyphenamate, Meprobamate, Phenoprobamate, Tybamate.

Others Alpidem, Benzoctamine, Captodiamine, Chlormezanone, Etifoxine, Fluoresone, Glutamic Acid, Hydroxyzine, Mecloralurea, Mephenoxalone, Oxanamide, Phenaglycodol, Suriclone.

BENZODIAZEPINE ANTAGONIST such as Flumazenil.

Bronchodilator

Ephedrine Derivatives such as Albuterol, Bambuterol, Bitolterol, Carbuterol, Clenbuterol, Clorprenaline, Dioxethedrine, Eprozinol, Etafedrine, Ethylnorepinephrine, Fenoterol, Hexoprenaline, Isoetharine, Isoproterenol, Mabuterol, Metaproterenol, N-Methylephedrine, Pirbuterol, Procaterol, Protokylol, Reproterol, Rimiterol, Soterenol, Terbutaline, Tulobuterol.

Quaternary Ammonium Compounds such as Flutropium Bromide, Oxitropium Bromide.

Xanthine Derivatives such as Acefylline piperazine, Acefylline Ambuphylline, Aminophylline, Bamifylline, Choline Theophyllinate, Doxofylline, Dyphylline, Enprofylline, Etamiphyllin, Etofylline, Guaithylline, Proxyphylline, Theobromine, 1-Theobromineaceatic Acid, Theophylline.

Others such as Methoxyphenanime, Tretoquinol.

Calcium Channel Blocker

Arylalkylamines such as Bepridil, Diltiazem, Fendiline, Gallopamil, Terodiline, Verapamil.

Dihydropyridine derivates such as Felodipine, Isradipine, Nicardipine, Nifedipine, Nilvadipine, Nimodipine, Nisoldipine, Nitrendipine Piperazine Derivatives Such as Flunarizine Others Such as Perhexiline.

CALCIUM REGULATOR such as Calcifediol, Calcitonin, Calcitriol, Clodronic Acid, Dihydrotachysterol, Elcatonin, Etidronic Acid, Ipriflavone, Pamidronic Acid, Parathyroid Hormone, Teriparatide Acetate.

CARDIOTONIC such as Acetyldigitoxins, 2-Amino 4-Picoline, Amrinone, Buclasdesine, Cerberoside, Camphotamide, Convallatoxin, Cymarin, Denopamine, Deslanoside, Digitalin, Digitalis, Digitoxin, Digoxin, Dobutamine, Dopamine, Dopexamine, Enoximone, Erythrophleine, Fenalcomine, Gitalin, Gitoxin, Glycocyamine, Heptaminol, Hydrastinine, Lanatosides, Metamivam, Substituted Methoxyphenyl-4,5-dihydro-3(2H)-pridazinones, Milrionone, Neriifolin, Oleandrin, Ouabain, Oxyfedrine, Prenalterol, Proscillaridin, Resibufogenin, Scillaren, Scillarenin, Strophanthin, Sulmazole, Theobromine, Xamoteroi.

CHELATING AGENT such as Deferoxamine, Edetate Calcium Disodium, Edetate Disodium, Edeate Sodium, Edetate Trisodium, Pentetate Calcium Trisodium, Pentectic Acid, Succimer, Trientine.

Cholecystokinin Antagonist (Proglumide)

CHOLELITHOLYTIC AGENT such as Chenodiol, Methyl tert-Butyl Ether, Monooctanoin, Ursodiol.

CHORETIC such as Alibendol, Anethole Trithion, Azintamide, Cholic Acid, Cicrotoic Acid, Clanobutin, Cyclobutyrol, Cyclovalone, Cynarin(e) Dehydrocholic Acid, Deoxycholic Acid, Dimecrotic Acid, d-Ethylbenzyl Alcohol, Exiproben, Feguprol, Fencibutirol, Fenipentol, Florantyrone, Hymecromone, Menbutone, 3-(OMethoxyphenyl)-2-Phenylacrylic Acid, Metochalcone, Moquizone, Osalmid, Ox Bile Extract, 4,4'-Oxydi-2-Butanol, Piprozolin, Prozapine, 4-Salicyloylmorpholine, Sincalide, Taurocholic Acid, Timonacic, Tocamphyl, Trepibutone, Vanitiolide.

CHOLINERGIC such as Aceclidine, Acetylcholine bromide, Acetylcholide, Aclatonium napadisilate, Benzpyrinium bromide, Bethanechol, Carbachol, Carpronium, Demecarium, Dexpanthenol, Diisopropyl Paraoxon, Echothiophate, Edrophonium, Eseridine, Furtrethonium, Isoflurophate, Methacholine chloride, Muscarine Neostigmine, Oxapropanium, Physostigmine, Pyridostigmine.

CHOLINESTERASE INHIBITOR such as Ambenonium, Distigmine, Galanthamine.

CHOLINESTERASE REACTIVATOR such as Obidoxime, Pralidoxime CNS STIMULANT/AGENT such as Amineptine, Amphetamine, Amphetaminil, Bemegride, Benzphetamine, Brucine, Caffeine, Chlorphentemine, Clofenciclan, Cloratermine, Coca, Demanyl Phosphate, Dexoxadrol, Dextroamphetamine Sulfate, Diethylpropion, N-Ethylamphetamine, Ethamivan, Fencamfamine, Fenethylline, Fenozolone, Flurothyl, Hexacyclonate Sodium, homocamfin, Mazindol, Mefexamide, Methamphetamine, Methylphenidate, Nicotine, Nicotinic agonist, Nikethamide, Pemoline, Pentylenetetrazole, Phenidimetrazine, Phenmetrazine, Phentermine, Picrotoxin, Pipradrol, Prolintane, Pyrovalerone, Terahydrobenzothienpphyridines.

DECONGESTANT such as Cafaminol, nordefrin

DENTAL CARRIES PROPHYLACTIC such as sodium fluoride.

DEPIGMENTOR such as Hydroquinine, Hydroquinone, Monobenzone

Diuretic

Organomercurials such as Chlormerodrin, Meralluride, Mercamphamide, Mercaptomerin Sodium, Mercumallylic Acid, Mercumatillin Sodium, Mercurous Chloride, Mersalyl.

Pteridines such as Furterene, Triamterene.

Purines such as 7-Morpholinomethyltheophylline, Pamabrom, Protheobromine, Theobromine Steroids such as Canrenone, Oleandrin, Spironolactone Sulfonamide Derivatives such as Acetazolamide, Azosemide, Bumetanide, Butazolamide, Chloraminophenamide, Clofenamide, Clorexolone, Diphenylmethane-4,4'-Disulfonamide, Disulfamide, Ethoxzolamide, Flumethiazide, Mefruside, Methazolamide, Piretamide Torasemide.

Uracils such as Aminometradine, Amisometradine

Others such as Amanozinde, Amiloride, Arbutin, Chlorazanit, Ethacrynic Acid, Etozolin, Isosorbide, Mannitol, Metochalcone, Perhexiline, Urea.

DOPAMINE RECEPTOR AGONIST such as Bromocriptine, Fenoldopam, Lisuride, Naxagolide, Pergolide.

ECTOPARASITICIDE such as Amitraz, Benzyl Benzoate, Carbaryl, Crotamiton, DDT, Dixanthogen, Isobornyl Thiocyanoacetate (Technical), Lime Sulfurated Solution Lindane, Malathion, Mercuric Oleate, Sulphur (Pharmaceutical).

Enzyme

Digestive such as—Amylase(Swine Pancreas), Lipase, Pancrelipase, Pepsin, Renin

Penicillin Inactivating such as Penicillinase

Proteolybc such as Collagenase, Chymopapain, Chymotrypsins, Papain, Trypsin

ENZYME INDUCER (HEPATIC) such as Flumecinol.

Estrogen

Nonsteroidal such as Benzestrol, Broparoestrol, Chlorotrianisene, Dienestrol, Diethylstilbestrol, Diethylstilbestrol Diprprionate, Dimestrol, Fosfestrol, Hexestrol, Methallenstril, Methestrol.

Steroidal such as Colpormon, Conjugated Estrogenic Hormones, equilenin, Equilin, Esterified Estrogens Estropipate, 17 β-Estradiol, Estradiol, estradiol Benzoate, Estradiol 17b-Cypionate, Estrone, Ethinyl Estradiol, Mestranol, Moxestrol, Mytatrienediol, Polyestradiol Phosphate, Quinestradiol, Quinestrol.

GASTRIC SECRETION INHIBITOR such as enterogastrone, Octreotide.

GLUCOCORTICOID such as 21-Acetoxypregnenolone, Alclometasone, Algestone, Amcinonide, Beclomethasone, Betamethasone, Betamethasone dipropionate, Budesonide, Chloroprednisone, Clobetasol, Clobetasone, Clocortolone, Cloprednol, Corticosterone, Cortisone, Cortivazol, Deflazacort, Desonide, Desoximetasone, Dexamethasone, Diflorasone, Diflucortolone, Difluprednate Enoxolone, Fluazacort, Flucloronide, Flumethasone, Flunisolide, Fluocinolone acetonide, Fluocinonide, Fluocortin butyl, Fluocortolone, Fluorometholone, Fluperolone acetate, Fluprednidene acetate, Fluprednisolone, Flurandrenolide, Formocortal, Halcinonide, Halometasone, Halopredone Acetate, Hydrocotramate, Hydrocortisone, Hydrocortisone Acetate, Hydrocortisone phosphate, Hydrocortisone 21-Sodium Succinate, Hydrocortisone Tebutate, Mazipredone, Medrysone, Meprednisone, Methylprednisolone, Mometasone furoate, Paramethasone, Prednicarbate, Prednisolone, Prednisolone 21-Diethylaminoacetate, Prednisolone Sodium Succinate, Prednisolone Sodium Phosphate, Prednisolone Sodium 21-mSulfobenzoate, Prednisolone 21-Stearoylglycolate, Prednisolone Tebutate Prednisolone 21-Trimethylacatate, Prednisone, Prednival, Prednylidene, Prednylidene 21-Diethylaminoacetate, Tixocortal, Triamcinolone, Triamcinolone acetonide, Triamcinolone benetonide, Triamcinolone hexacetonide, GONAD-STIMULATING PRINCIPLE such as Clomiphene, Cyclofenil, Epimestrol, FSH, HCG, LH-RH.

GONADOTROPIC HORMONE such as LH, PMSG
GROWTH HORMONE INHIBITOR such as Somatostatin
GROWTH HORMONE RELEASING FACTOR such as Sermorelin
GROWTH STIMULANT such as Somatotropin
HEMOLYTIC such as Phenylhydrazine
HEPARIN ANTAGONIST such as Hexadimethrine Protamines.

HEAPATOPROTECTANT such as Betaine, Citiolone, Malotilate, Orazamide, Phosphorylcholine, Protoporphyrin IX, Silymarin-Group, Thioctic Acid, IMMUNOMODULATOR such as Amiprilose, Bucillamine, Ditiocarb Sodium, Inosine Pranobex, Muroctasin, Platonin, Procodazole, Tetramisole, 6-Aryl-1-5-6-Digydroimidazol-(2,1-B) Thiazole Derivatives, Thymomodulin, Thymopentin.

IMMUNOSUPPRESSANT such as Cyclophilin, Cyclosporins, FK-506, Mizoribine, Rapamycin, Rapamycin Sulfamates IONEXCHANGE RESIN such as Carbacrylic Resins, Resodec, Sodium Polystyrene Sulfonate LACTATION STIMULATING HORMONE such as Prolactin LH-RH AGONIST such as Buserelin, Goserelin, Leuprolide, Nafarelin, Triptorelin.

LIPOTROPIC such as N-Acetylmethionine, Choline Chloride, Choline Dehydrocholate, Choline Dihydrogen Citrate, Inositol, Lecithin, Methionine LUPUS ERYTHEMATOSUS SUPPRESSANT such as Bismuth Sodium Triglycollamate, Bismuth Subsalicylate.

MINERALOCORTICOID such as Aldosterone, Deoxycorticosterone, Fludrocortisone.

MIOTIC such as Pilocarpus
MONOAMINE OXIDASE INHIBITOR such as Phenoxypropazine, Pivyalylbenzhydrazine MUCOLYTIC such as Acetylcysteine, Bromhexine, Carbocysteine, Domiodol, Letosteine, Mecysteine, Mesna, Sobrerol, Stepronin, Tiopronin, Tyloxapol MUSCLE RELAXANT (SKELETAL) such as Afloqualone, Alcuronium, Atracurium Besylate, Baclofen, Benzoquinonium, C-Calebassine, Carisoprodol, Chlorphenesin Carbamate, Chlorzoxazone, Curare, Cyclobenzaprine, dantrolene, Decamethonium, Eperisone, Fazadinium, Flumetramide, Gallamine triethiodide, Hexacarbacholine, Hexafluorenium, Idrocilamide, Laudexium Methyl Sulfate, Leptodactyline, Memantine, Mephenesin, Metaxalone, Methocarbamol, Metocurine Iodide, Pancuronium, Pipecurium, Promoxolane, Quinine Sulfate, Styramate, Succinylcholine, Succinylcholine Suxethonium Bromide, Tetrazepam, Thiocolchicoside, Tizanidine, Tolperisone, Tubocurarine, Vecuronium, Zoxazolamine.

NARCOTIC ANTAGONIST such as Amiphenazole, Cyclazocine, Levallorphan, Nadide, Nalmafene, Nalorphine, Nalorphine Dinicotinate, Naloxone, Naltrexone.

NEUROPROTECTIVE such as Dizocilpine

NOOTROPIC such as Aceglutamide, Acetylcarnitine, Aniracetam, Bifemelane, Exifone, Fipexide, Idebenone, Indeloxazine, Nizofenone, Oxiracetam, Piracetam, Propentofylline, Propentofylline Pyritinol OPHTHALMIC AGENT such as 15-ketoprostaglandins.

Ovarian Hormone such as Relaxin

OXYTOCIC such as Carboprost, Cargutocin, Deaminooxytocin, Ergonovine, Gemeprost, Methylergonovine, Oxytocin, Pituitary (Posterior), Prostaglandin E2, Prostagandin F2a, Sparteine.

PEPSIN INIBITOR such as Sodium Amylosulfate
PERISTALTIC STIMULANT such as Cisapride
PROGESTOGEN such as Allylestrenol, Anagestone, Chlormadinone Acetate, delmadinone Acetate, Demegestone, Desogestrel, Dimethisterone, Dydrogesterone, Ethinylestrenol, Ethisterone, Ethynodiol, Ethynodiol Diacetate, Flurogestone Acetate, Gestodene, Gestonorone Caproate, Haloprogesterone, 17-Hydroxy-16-methylene-progesterone, 17-Hydroxyprogesterone, 17a-Hydroxygesterone Caproate, Lynestrenol, Medrogestone, Medroxyprogesterone, Megestrol acetate, Melengestrol, Norethindrone, Norethindrone Acetate, Norethynodrel, Norgesterone, Norgestimate, Norgestrel, Norgestrienone, 19-Norprogesterone, Norvinisterone, Pentagestrone, Progesterone, Promegestone, Quingestrone, Trengestone PROLACTIN INHIBITOR such as Metegoline
PROSTAGLANDIN/PROSTAGLANDIN ANALOG such as Beraprost, Prostacyclin, Prostaglandin E1, Suiprostone PROTEASE INHIBITOR such as Aprotinin, Camostat, Gabexate, Nafamostat RESPIRATORY STIMULANT such as Almitrine, Dimefline, Dimorpholamine, Doxapram, Lobeline, Mepixanox, Pimeclone, Sodium succinate, Tacrine SCLEROSING AGENT such as Ethanolamine, Ethylamine, 2-Hexyldecanoic Acid, Sodium Ricinoleate, Sodium Tetradecyl Sulfate, Tribenoside Sedative/Hypnotic Acyclic Ureides such as Acecarbromal, Apronalide, Bromisovalum, Capuride, Carbromal, Ectylurea, Alcohols such as Chlorhexadol, Ethchlorvynol, 4-Methyl-5-thiazoleethanol, Tert-Pentyl Alcohol, 2,2,2,-Trichloroethanol Amides such as Butoctamide, Diethylboromoacetamide, Ibrotamide, Isovaleryl Diethylamide, Niaprazine, Tricetamide, Trimetozine, Zolpidem, Zopiclone, Barbituric Acid Derivatives Such as Allobarbital, Amobarbital, Aprobarbital, Barbital, Brallobarbital, Butabarbital sodium, Butalbital, Butallylonal, Butethal, Carbubarb, Cyclobarbital, Cyclopentobarbital, Enallylpropymal, 5-Ethyl-5-(1-Piperidyl) Barbituric Acid, 5-Furfuryl-5-isopropylbarbituric Acid, Heptabarbital, Hexethal sodium, Hexobarbital, Mephobarbital, Methitural, Narcobarbital, Nealbarbital, Pentobarbital Sodium, Phenallymal, Phenobarbital, Phenobarbital Sodium, Phenylmethylbarbituric Acid, Probarbital, Propallylonal, Proxibarbal, Reposal, Secobarbital Sodium, Talbutal, Tetrabarbital, Vinbarbital Sodium, Vinylbital Benzodiazepine Derivatives such as Brotizolam, Doxefazepam, Estazolam, Flunitrazepam, Flurozepam, Heloxazolam, Loprazolam, Lormetazppam, Nitrazepam, Quazepam, Temazepam, Triazolam Bromides such as Ammonium Bromide, Calcium Bromide, Calcium Bromolactobionate, Lithium Bromide, Magnesium Bromide, Potassium Bromide, Sodium Bromide Carbamates such as Amyl Carbamate(Tertiary), Ethinamate, Hexapropymate, Meparfynol carbamate, Novonal, Trichlorourethan Chloral Derivatives such as Carboclural, Chloral Betaine, Chloral Formamide, Chloral Hydrate, Chloralantipyrine, Dichloralphenazone, Pentaerythritol Chloral, Triclofos Piperidinediones such as Glutethimide, Methyprylon, Piperdione, Pyrithyldione, Taglutimide, Thalidomide Quinazolone Derivatives such as Etaqualone, Mecloqualone, Methaqualone Others such as Acetal, Acetophenone, Aldol, Ammonium Valerate, Amphenidone, d-Bornyl a-Bromoisovalerate, d-Bornyl Isovalerate, Bromoform, Calcium 2-Ethylbutanoate, Carfinate, α-Chloralose, Clomethiazole, Cypripedium, doxylamine, Etodroxizine, Etomidate, Fenadiazole, Homofenazine, Hydrobromic Acid, Mecloxamine, Menthyl Valerate, Opium, Paraldehyde, Perlapine, Propiomazine, Rilmazafone, Sodium Oxybate, Sulfonethylmethane, Sulfonmethane THROMBOLYTIC such as APSAC, Plasmin, Pro-Urokinase, Streptokinase, Tissue Plasminogen Activator, Urokinase THYROTROPIC HORMONE such as TRH, TSH MISCELLANEOUS—Viatamins, Mineral as well as other Nutrients, Vit B1, B2, B6, B12 and other water soluble vitamins, Vitamin C, Vitamin A,D,E and other oil soluble Vitamins, Iron, Zinc and other Miconutrinets and their combinations with Vitamins, Antioxidants i.e. Betavarotene and combination thereof with Vitamins, Ginseng and other rejuvenants and suitable combinations of drugs disclosed above.

The suitable mucoadhesive agents include cellulose derivatives like methyl cellulose, hydroxypropylmethyl cellulose, hydroxypropyl cellulose, cellulose acetate phthalate, cellulose acetate, cellulose acetate butyrate, cellulose acetate propionate, cellulose acetate trimelliate, cellulose carboxymethyl ethers and their salts, hydroxypropylmethyl cellulose phthalate, hydroxypropylmethyl cellulose acetate succinate, polyethylene, polyvinyl acetate (homopolymer), polyvinyl acetate phthalate, propylene glycolalginate, PVMI/MA copolymer, PVP/dirnethiconylacrylate/polycarbamyl/polyglycolester, PVP/dimethylaminoethylmethacrylate/polycarbamyl polyglycol ester, PVP/polycarbamyl polyglycol ester, PVPNA copolymer, gelatin and Gelatin derivatives.

Alginates, Carbomers, Polycarbophils.

Methacrylic acid copolymers.

Carrageenans, pentins, chitosans, cyclodextrins, lecitins.

Natural gums containing galactomannans like xanthan gum, Acacia, tragacanth, agar, guar gum and the like.

The fast soluble part of the sweetener gives a rapid burst of the sweetness whereas the mucoadhesive form binds to the oral mucosa and gives a prolonged sweet taste thereby effectively masking the bitter or bad after-taste of the pharmaceutically active agents.

The conventional therapeutically acceptable additives like binding agents, lubricants, disintegrants, flavouring agents, colouring agents, pH modifiers and wetting agents may be added to the pharmaceutical composition prepared.

If desired, the active pharmaceutical agent may be first subjected to the conventional taste neutralization treatment like forming matrix microspheres, microencapsulation, complexation and the like.

The compressed tablets have sufficient mechanical strength which allows them to be packed in normal push-through type blister packages and does not require special packaging like peel-off blisters.

The manufacturing process is exemplified below:

EXAMPLE 1

Step 1: Preparation of Non-Sugar Sweetener in Mucoadhesive Form.

| | |
|---|---|
| Aspartame | 20.00 g |
| PVM/MA Copolymer (Gantrez AN 169) | 0.40 g |
| Acetone | 20.00 ml |

Dissolve Gantrez AN 169 in 20 ml Acetone. Granulate Aspartame with this solution and dry at 40° C. Sift through 60 mesh sieve.

Step 2: Tablet Formulation

| | |
|---|---|
| Nimesulide (Pharmaceutically active agent) | 100.0 mg |
| Mannitol | 204.5 mg |
| Aspartame of step 1 in mucoadhesive form | 7.0 mg |
| Flavour | 1.5 mg |
| Sodium Starch Glycolate | 3.0 mg |
| Magnesium Stearate | 4.0 mg |

Sift all the ingredients through 40 mesh sieve and blend. Compress into tablets at a hardness of 1 to 5 Kg.

EXAMPLE 2

Step 1: Preparation of Non-Sugar Sweetener in Mucoadhesive Form:

| | |
|---|---|
| Aspartame | 20.00 g |
| Carbomer (Carbopol 934P) | 0.40 g |
| Water | 20.00 ml |

Disperse Carbopol 934P in 20 ml Water. Granulate Aspartame with it and dry at 40° C. Sift through 60 mesh sieve.

Step 2: Tablet Formulation

| | |
|---|---|
| Nimesulide (Pharmaceutically active agent) | 100.0 mg |
| Mannitol | 204.5 mg |
| Aspartame | 3.0 mg |
| Aspartame of step 1 in mucoadhesive form | 4.0 mg |
| Flavour | 1.5 mg |
| Sodium Starch Glycolate | 3.0 mg |
| Magnesium Stearate | 4.0 mg |

Sift all the ingredients through 40 mesh sieve and blend. Compress into tablets at a hardness of 1 to 5 Kg.

EXAMPLE 3

Step 1: Taste Neutralization of Drug Substance.

| | |
|---|---|
| Ibuprofen (Pharmaceutically active agent) | 95.95 g |
| Tribehenin | 4.00 g |
| Polysorbate 80 | 0.05 g |
| Water | 40.00 ml |

Heat water to about 50° C.–60° C. Add polysorbate 80 and mix. Under stirring add Tribehenin followed by Ibuprofen. A Wet dough will be formed. Cool it to 35° C. Size it through 20 mesh sieve. Dry at about 45° C. till moisture content is 1 to 3%. Sift through 60 mesh sieve.

Step 2: Tablet Formulation

| | |
|---|---|
| Ibuprofen from step 1 Equivalent to Ibuprofen | 200.0 mg |
| Xylitol | 204.5 mg |
| Aspartame in mucoadhesive form (from step 1 of example 2) | 7.00 mg |
| Flavour | 1.5 mg |
| Sodium Starch Glycolate | 3.0 mg |
| Megnesium Stearate | 4.0 mg |

Sift all the ingredients through 40 mesh sieve and blend. Compress into tablets at a hardness of 1 to 5 Kg.

EXAMPLE 4

| | % w/w |
|---|---|
| Cisapride (Pharmaceutically active agent) | 2.50 |
| Liquid Paraffin | 0.25 |
| Sorbitol | 84.75 |
| Sodium Starch Glycollate | 5.00 |
| Croscarmellose Sodium | 1.25 |
| Magnesium Stearate | 1.25 |
| Aspartame in mucoadhesive form (from step 1 of example 1) | 3.00 |
| Colloidal Silicon Dioxide | 1.25 |
| Flavour | 0.75 |

Pass the drug through mesh no. 60 (BSS) sieve. Granulate the drug with a solution of Liquid Paraffin in Dichloromethane and pass through mesh no. 40(BSS) sieve. Dry at a temperature of 45–50° C. Sift Sorbitol through mesh no. 60(BSS) sieve and mix with drug containing Liquid Paraffin. This blend is then granulated with water and then dried at a temperature of 50–60° C. The dried granules are sifted through mesh no. 22(BSS) sieve.

Sift Sodium Starch Glycollate, Magnesium Stearate, Colloidal Silicon Dioxide, Crosscarmellose Sodium, Aspartame (in mucoadhesive form) and Flavours through mesh no. 30 (BSS) sieve and mix with the above said bulk. Compress into tablets using conventional tabletting machine at a hardness of 1–3 Kg.

EXAMPLE 5

| | % w/w |
|---|---|
| Cetirizine Dihydrochloride (Pharmaceutically active agent) | 2.5 |
| Crosslinked Polyacrylic Acid (Ion-exchange resin) | 10.0 |
| Hydrochloric Acid | q.s. to adjust pH |
| Mannitol | 64.5 |
| Croscarmellose Sodium | 3.75 |

-continued

| | % w/w |
|---|---|
| Povidone | 0.25 |
| Aspartame in mucoadhesive form (from step 1 of example 1) | 6.25 |
| Magnesium Stearate | 0.50 |
| Aerosil | 0.75 |
| Sodium Starch Glycollate | 3.75 |
| Sodium Chloride | 3.00 |
| Citric Acid | 2.00 |
| Flavour | 2.75 |

Dissolve Cetirizine dihydrochloride in 20 times of its weight of water. Add Crosslinked Poiyacrylic Acid in small increments with constant stirring. Adjust pH to 3 with hydrochloric acid. Keep aside for 1 to 6 hours and then decant the water. Wash the sediment with water at least twice. Dry the sediment at 40 to 50° C. Pass through sieve of mesh no 60 (BSS). Mix with pre-sifted (through mesh no. 30BBS) blend of Mannitoi, Croscarmeilose Sodium, Povidone, Aspartame (in mucoadhesive form), Magnesium Stearate, Aerosil, Sodium Starch Glycollate, Sodium Chloride, Citric Acid and Flavour. Compress into tablets using conventional tabletting machine at a hardness of 1–3 kg.

EXAMPLE 6

Step 1. Preparation of Non-Sugar Sweetener in Mucoadhesive Form:

| | |
|---|---|
| Saccharin Sodium | 100.00 g |
| Polycarbophil (Noveon AA-1) | 4.00 g |
| Water | 10.00 g |

Disperse Polycarbophil in Water. Granulate Saccharin Sodium with this dispersion. Dry at 50° C. and sift through mesh no. 40 (BSS).

Step 2.

| | % w/w |
|---|---|
| Chloroquine Phosphate (Pharmaceutically active agent) | 10.0 |
| Crosslinked Polyacrylic Acid, Potassium salt (Ion-exchange resin) | 20.0 |
| Hydrochloric Acid | q.s. to adjust pH |
| Mannitol | 51.50 |
| Crosscarmellose sodium | 3.50 |
| Povidone | 1.00 |
| Saccharin Sodium in mucoadhesive form (from step 1 of example 6) | 2.00 |
| Magnesium Stearate | 0.50 |
| Sodium Starch Glycollate | 3.75 |
| Sodium Chloride | 3.00 |
| Citric Acid | 2.00 |
| Flavour | 2.75 |

Dissolve Chloroquine Phosphate in 20 times of its weight of water. Add Crosslinked Polyacrylic Acid in small increments with constant stirring. Adjust pH to 6 with hydrochloric acid. Keep aside for 1 to 6 hours and then decant the water. Wash the sediment with water at least twice. Dry the sediment at 400 to 50° C. Pass through sieve of mesh no 60 (BSS). Mix with pre-sifted (through mesh no. 30 BSS) blend of Mannitol, Povidone, Saccharin Sodium (in mucoadhesive form), magnesium Stearate, Sodium

EXAMPLE 7

Step 1: Taste Neutralization of Drug Substance.

| | |
|---|---|
| Ascorbic Acid | 96.00 g |
| Gelatin | 4.00 g |
| Water | 30.00 ml |

Heat water to about 60° C.–70° C. Add Gelatin and dissolve. Coat the Ascorbic Acid by spraying the gelatin solution using fluidized bed coater. Size the coated drug powder through 40 mesh sieve.

Step 2: Mucoadhesive Sweetener.

| | |
|---|---|
| Ammonium Glycirrhizinate | 20.00 g |
| PVM/MA Copolymer (Gantrez AN 169) | 0.40 g |
| Acetone | 20.00 ml |

Dissolve Gantrez AN 169 in 20 ml Acetone. Granulate Ammonium Glycirrhizinate with this solution and dry at 40° C. Sift through 60 mesh sieve.

Step 3: Tablet Formulation

| | |
|---|---|
| Ascorbic Acid from step 1 | |
| Equivalent to Ascorbic Acid | 100.0 mg |
| Sorbitol | 204.5 mg |
| Ammonium Glycirrhizinate in Mucoadhesive form (from step 2) | 7.00 mg |
| Flavour | 1.5 mg |
| Sodium Starch Glycolate | 3.0 mg |
| Magnesium Stearate | 4.0 mg |

Sift all the ingredients through 40 mesh sieve and blend. Compress into tablets at a hardness of 1 to 5 Kg.

EXAMPLE 8

Tablet Formulation

| | |
|---|---|
| Interferon (Alpha) equivalent to | 18 Million I.U. |
| Mannitol | 204.5 mg |
| Aspartame in mucoadhesive form (from step 1 of example 1) | 7.0 mg |
| Flavour | 1.5 mg |
| Sodium Starch Glycolate | 3.0 mg |
| Magnesium Stearate | 4.0 mg |

Sift all the ingredients through 40 mesh sieve and blend. Compress into tablets at a hardness of 1 to 3 Kg.

EXAMPLE 9

| | |
|---|---|
| Alprazolam | 1 mg |
| Isomalt | 98.9 mg |
| Aspartame | 0.03 mg |
| Acesulfame potassium | 0.03 mg |
| Neohesperidine in Mucoadhesive form | 0.04 mg |

Procedure

Prepare the non-sugar sweetener neohesperidine in mucoadhesive form similar to as mentioned in the process for preparation of the non-sugar sweetener aspartame in said form (from step 1 of example 1). Sift all the ingredients through 30 mesh sieve and blend. Compress into tablets at a hardness of 1 to 3 Kg.

The advantages of the present invention are:

a. The pharmaceutical tablets prepared according to the present invention dissolve/disperse in the mouth within one minute requiring very little amount of body fluids like saliva to produce a solution or suspension of the drug for oral administration.

b. The tablet leaves a prolonged sweet taste in the mouth.

c. The unpleasant or bitter taste of the drug is masked without significantly interfering with the dissolution and ultimate bioavailability of the drug present in the tablet.

d. The process of this invention has low manufacturing cost avoiding the special and costly techniques like Lyophilization, Spray-drying and the like.

Since many apparently different embodiments of the present invention could be made without departing from the spirit and scope thereof, it is intended that the description of the invention herein be interpreted as being illustrative only and not limiting in any manner whatsoever.

We claim:

1. A fast dissolving pharmaceutical composition in solid dosage form with a prolonged sweet taste which consists essentially of:

a) at least one pharmaceutically active agent in an amount of from 0.1 to 99 weight % of the total dosage form;

b) at least one water soluble sugar in an amount of from 40 to 95 weight % of the total dosage form;

c) at least one non-sugar sweetener in a fast release form in an amount of from greater than 0 to 10 weight % of the total dosage form; and d) at least one non-sugar sweetener in a mucoadhesive slow release form in an amount of from 0.5 to 20 weight % of the total dosage form.

2. The composition according to claim 1, wherein the water soluble sugar is selected from the group consisting of mannitol, sorbitol and xylitol.

3. The composition as claimed in claim 1, wherein the non-sugar sweetener is selected from the group consisting of isomalt, aspartame, acesulfame potassium, saccharine sodium, cyclamates, neohesperidine and glycirrhizin.

4. A process for the preparation of a fast dissolving pharmaceutical composition according to claim 1, which consists essentially of mixing the following ingredients:

a) at least one pharmaceutically active agent in an amount of from 0.1 to 99 weight % of the total dosage form;

b) at least one water soluble sugar in an amount of from 40 to 95 weight % of the total dosage form;

c) at least one non-sugar sweetener in a fast release form in an amount of from greater than 0 to 10 weight % of the total dosage form; and d) at least one non-sugar sweetener in a mucoadhesive slow release form in an amount of from 0.5 to 20 weight % of the total dosage form;

and compressing the resulting mixture into the a solid dosage form.

5. The process according to claim 4 wherein the solid dosage form is a tablet.

6. The process according to claim 4, wherein the water soluble sugar is selected from the group consisting of mannitol, sorbitol and xylitol.

7. The process as claimed in claim 4, wherein the non-sugar sweetener is selected from the group consisting of isomalt, aspartame, acesulfame potassium, saccharine sodium, cyclamates, neohesperidine and glycirrhizin.

* * * * *